United States Patent [19]

Heinzmann et al.

[11] Patent Number: 5,772,637
[45] Date of Patent: Jun. 30, 1998

[54] INTRAVENOUS-LINE FLOW-CONTROL SYSTEM

[75] Inventors: R. Kurt Heinzmann, Francestown; Richard Lanigan, Concord; Peter Lund, Nashua; Dean L. Kamen, Bedford; William T. Larkins, Manchester; Robert Manning, Pembroke, all of N.H.

[73] Assignee: DEKA Products Limited Partnership, Manchester, N.H.

[21] Appl. No.: 472,212

[22] Filed: Jun. 7, 1995

[51] Int. Cl.$^6$ .................................................. A61M 5/00
[52] U.S. Cl. .............................. 604/248; 604/32; 604/49; 128/DIG. 12
[58] Field of Search ..................... 604/248, 246, 604/149–152, 28, 30, 32, 49–52, 80; 128/DIG. 12

[56] References Cited

U.S. PATENT DOCUMENTS

| | | | |
|---|---|---|---|
| 4,137,915 | 2/1979 | Kamen | 128/214 |
| 4,391,600 | 7/1983 | Archibald | 604/153 |
| 4,519,792 | 5/1985 | Dawe | 604/152 |
| 4,527,588 | 7/1985 | Tseo et al. | 137/565 |
| 4,585,441 | 4/1986 | Archibald | 604/245 |
| 4,586,691 | 5/1986 | Kozlow | 251/7 |
| 4,605,396 | 8/1986 | Tseo et al. | 604/32 |
| 4,689,043 | 8/1987 | Bisha | 604/250 |
| 4,818,190 | 4/1989 | Pelmulder et al. | 417/360 |
| 4,927,411 | 5/1990 | Pastrone et al. | 604/65 |
| 4,944,485 | 7/1990 | Daoud et al. | 251/9 |
| 5,005,604 | 4/1991 | Aslanian | 604/248 X |
| 5,017,192 | 5/1991 | Dodge et al. | 604/250 |
| 5,190,527 | 3/1993 | Hamilton et al. | 604/153 |
| 5,241,985 | 9/1993 | Faust et al. | 137/505.13 |
| 5,257,978 | 11/1993 | Haber et al. | 604/250 |
| 5,300,044 | 4/1994 | Classey et al. | 604/250 |
| 5,336,174 | 8/1994 | Daoud et al. | 604/30 |
| 5,364,364 | 11/1994 | Kasvikis et al. | 604/151 |

FOREIGN PATENT DOCUMENTS

| | | |
|---|---|---|
| 0314306A2 | 5/1989 | European Pat. Off. . |
| 0319278A1 | 6/1989 | European Pat. Off. . |
| 0450736A1 | 10/1991 | European Pat. Off. . |
| 0 510 881 A2 | 4/1992 | European Pat. Off. . |

*Primary Examiner*—John D. Yasko
*Attorney, Agent, or Firm*—Bromberg & Sunstein LLP

[57] ABSTRACT

An intravenous-line flow-control system for receiving a disposable cassette disposed in the intravenous line. The system prevents the free flow of intravenous fluid through the cassette when the cassette is removed from the system. The system includes a control unit having a door or similar structure for holding the cassette against a receiving surface. The control unit includes a stepper motor and a transmission member for turning a rotatable control valve on the cassette in order to restrict variably the flow of fluid through the cassette. When the door is being opened but while the cassette is still held against the receiving surface, a motor-disengagement mechanism moves at least the transmission member, and preferably the stepper motor as well, from a first position, from which the control valve may be engaged by the transmission member, to a second position, in which the transmission member is disengaged from the control valve. Preferably, the motor-disengagement mechanism includes a button on the handle of a door-opening mechanism, and by pushing the button the transmission member and the stepper motor are moved to the second position. In addition, when the door is being opened but while the cassette is still held against the receiving surface, a shut-off mechanism engages the cassette's control valve and turns the control valve to its closed position. The control unit may use alternative power supplies and include links for communicating with other control units.

12 Claims, 11 Drawing Sheets

INTRAVENOUS-LINE FLOW-CONTROL SYSTEM

RELATED APPLICATIONS

Filed concurrently herewith are applications Ser. No. 08/478065, entitled "Cassette for Intravenous-Line Flow-Control System" for an invention by Houle and Larkins Ser. No. 08/48606 entitled "Intravenous-Line Air-Elimination System" for an invention by Manning, Larkins, Houle, Kamen and Faust and Ser. No. 08/477380 entitled "Intravenous-Line Air-Detection System" for an invention by Larkins, Beavis and Kamen All of these related applications are incorporated herein by reference.

TECHNICAL FIELD

The present invention relates to apparatus and methods for controlling flow through an intravenous line, and preventing free flow of intravenous fluid through the line when the line, and in particular a cassette disposed in the line, is removed from a control unit that interacts with the cassette.

SUMMARY OF THE INVENTION

The present invention is directed to an intravenous-line flow-control system for receiving a disposable cassette disposed in the intravenous line. The system prevents the free flow of intravenous fluid through the cassette when the cassette is removed from the system. The system includes a control unit having a housing, which has a receiving surface against which the cassette is placed.

The housing has a door or similar structure for holding the cassette against the receiving surface when the door is closed and for allowing removal of the cassette when the door means is opened. A mechanism for opening the door, preferably a handle that may be rotated, causes the opening of the door when the mechanism is actuated (e.g., when the handle is turned).

The control unit includes means for turning a rotatable control valve on the cassette in order to restrict variably the flow of fluid through the cassette. Preferably, the turning means including a stepper motor and a transmission member, which can engage the control valve to transmit torque from the motor to the control valve. The transmission member, and preferably the stepper motor as well, are movably mounted within the control unit, so as to be able to move from a first position, from which the control valve may be engaged, to a second position, in which the transmission member is disengaged from the control valve.

A motor-disengagement mechanism moves at least the transmission member, and preferably the stepper motor as well, from the first to the second position when the door-opening mechanism is being actuated but while the cassette is still held against the receiving surface, Preferably, the motor-disengagement mechanism includes a button on the handle of the door-opening mechanism, and by pushing the button the transmission member and the stepper motor are moved to the second position. The motor-disengagement mechanism is preferably linked with the door-opening mechanism, so that the handle cannot be turned enough to open the door completely until the button is pushed.

The system also includes a shut-off mechanism, connected to the door-opening mechanism, for engaging, when the door-opening mechanism is being actuated but while the cassette is still held against the receiving surface, the cassette's control valve and turning the control valve to its closed position. In the preferred embodiment, the shut-off mechanism includes a gear that can engage the outer circumference of the control valve's control wheel. After the turning means is disengaged from the control valve, this gear is turned by the turning of the handle so as to turn the control valve to its closed position.

The mechanisms for opening the door preferably work in the following manner:

first, the button of motor-disengagement mechanism is pushed, causing (i) the transmission member to become disengaged from the cassette, (ii) the shut-off mechanism to become engaged with the door-opening mechanism, and (iii) allowing the handle to be turned (in the manner set forth in the next two steps);

second, the handle may be turned to cause the gear of the shut-off mechanism to turn the cassette's control wheel to the closed position; and third, the handle is turned further causing the door to open.

In one embodiment, the button is pushed by a user wishing to open the door and remove the cassette. In another embodiment, the handle includes a cam that pushes the button automatically as one turns the handle.

Preferably, the motor-disengagement mechanism includes means to keep the turning means in the second position while the handle is being turned to open the door, but preferably allows the turning means to return to the first position after the door means is fully opened. This is accomplished preferably by using first and second complementing keys, the first key being attached to and rotating with the handle, the second key being attached to and moving with the button, so that (i) when the process begins the first and second keys are in complementary engagement, (ii) when the button is pushed, the first and second keys become disengaged, and (iii) when the handle is turned to open the door, the first key is turned with respect to the second key, so that the keys are in interfering relation with each other. The first and second keys are shaped so that, when the door is fully open, the first and second keys return to complementary engagement with each other, so as to permit the turning means to return to the first position.

Preferably, the cassette's rotatable valve has a control wheel with first and second engaging means. The first engaging means is capable of being engaged by the gear of the shut-off mechanism, the first engaging means including a plurality of teeth closely located with respect to each other and evenly distributed around the circumference of the control wheel, except for a sector of the circumference that lacks teeth. The second engaging means is capable of being engaged by the transmission member of the turning means. The sector of the control wheel's circumference that lacks teeth is located so that, when the valve is in its fully closed position, the sector lacking teeth is adjacent the shut-off mechanism's gear, so that the shut-off mechanism does not continue turning the control wheel after the valve is fully closed.

Other novel aspects of the control unit involve the use of alternative power supplies and communication amongst a plurality of control units to control a plurality of lines leading to the same patient. In one preferred embodiment, the control unit includes AC means for receiving AC power from a wall outlet and converting the AC power to DC power, which is connected to the control unit housing by a first cord for carrying DC power, and further includes DC means for receiving DC power from a second control unit mounted on the same pole, wherein the second control unit is connected to a wall outlet, the DC means including a second cord for carrying DC power. The second cord may include additional wires for carrying electrical signals between the control units. The control unit also preferably includes internal-battery means for providing DC power when the AC means is disconnected from the wall outlet, the internal battery means being located inside the housing, and external-battery-receiving means for permitting an external battery pack to be connected to the housing's exterior to provide power to the control unit in lieu of AC power from a wall outlet and from the internal-battery means.

Figure 5B:
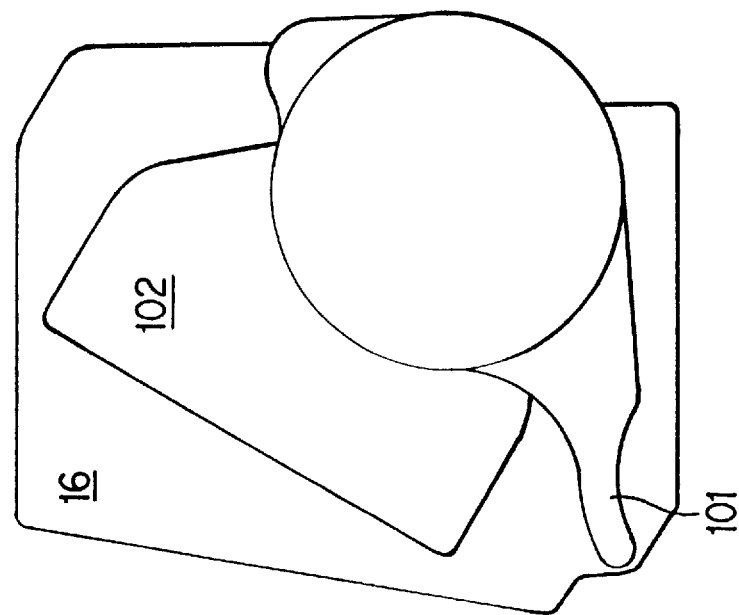
FIG. 5A shows the mechanisms of the FIG. 1 control unit during normal operation.
Figure 5A:
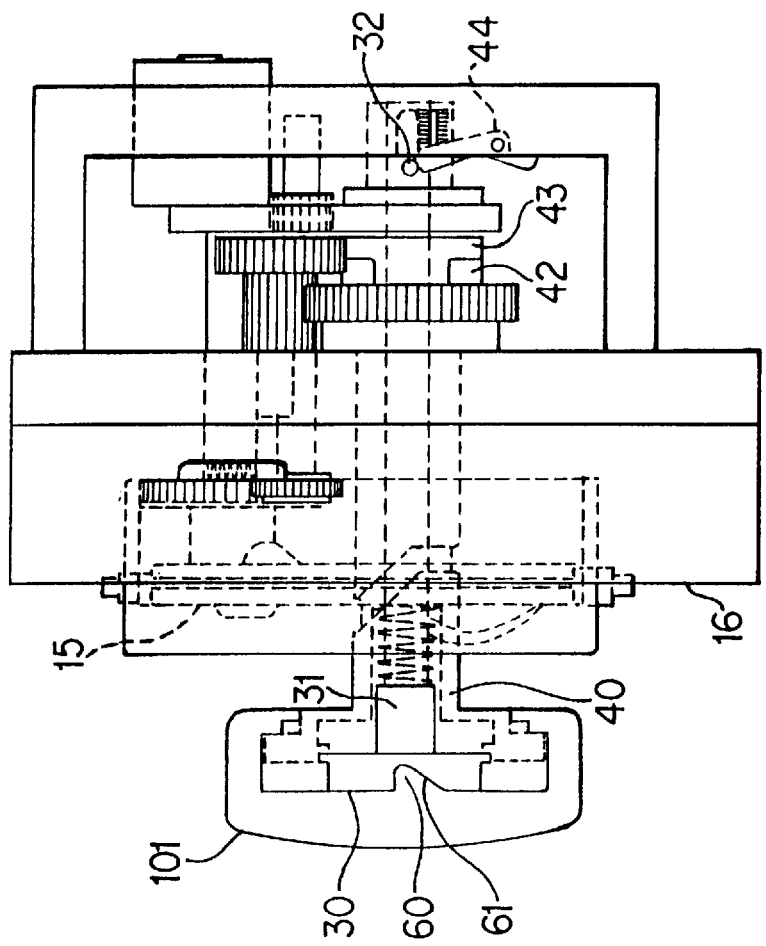

FIG. SB shows the position of the handle of the FIG. 5A control unit during normal operation.

Figure 6B:
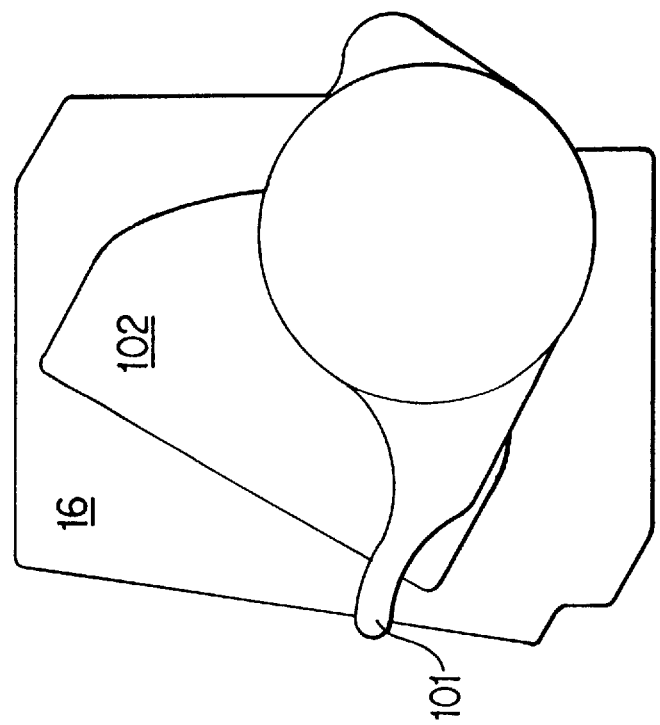
Figure 6A:
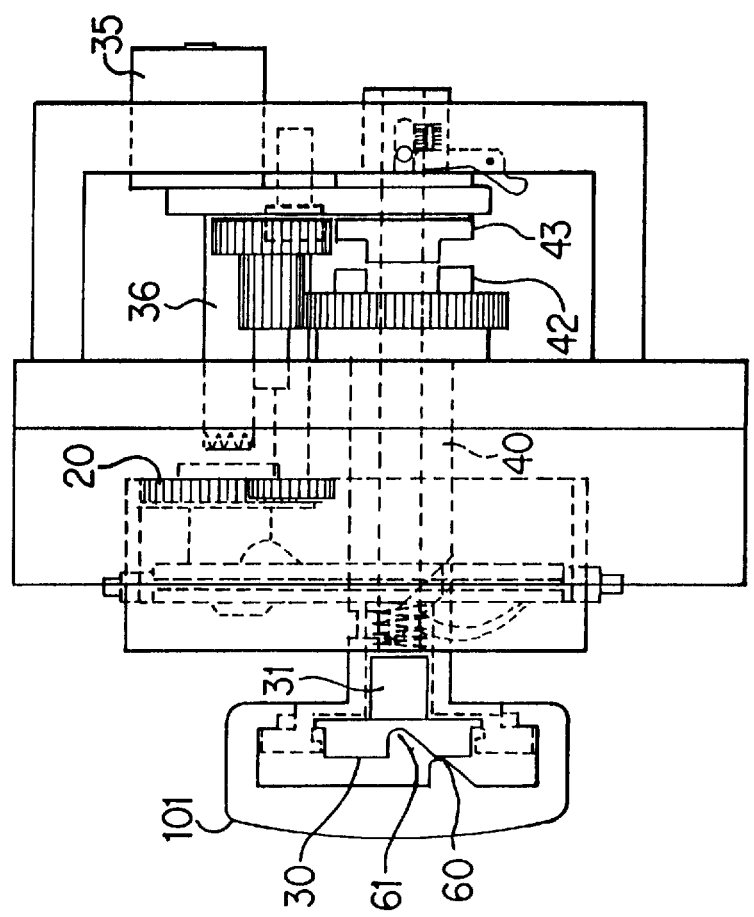

FIG. 6A shows the position of the mechanisms after the first step of opening the door of the FIG. 5A control unit.

FIG. 6B shows the position of the handle in the control unit of FIG. 6A.

Figure 7B:
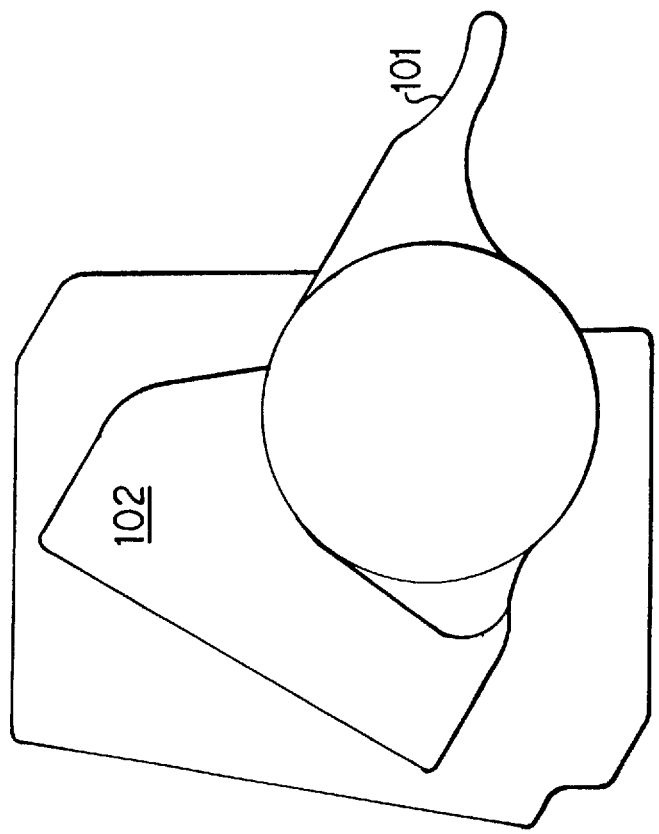
Figure 7A:
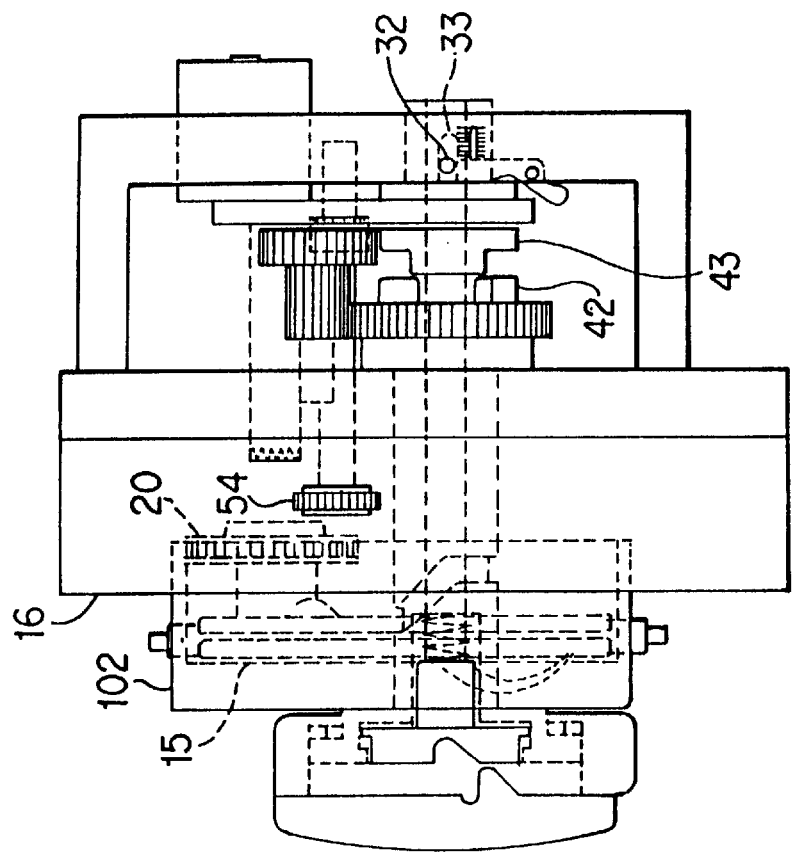

FIG. 7A shows the position of the mechanisms after the door of the FIG. 5A control unit has been fully opened.

FIG. 7B shows the position of the handle in the control unit of FIG. 7A.

Figure 8B:
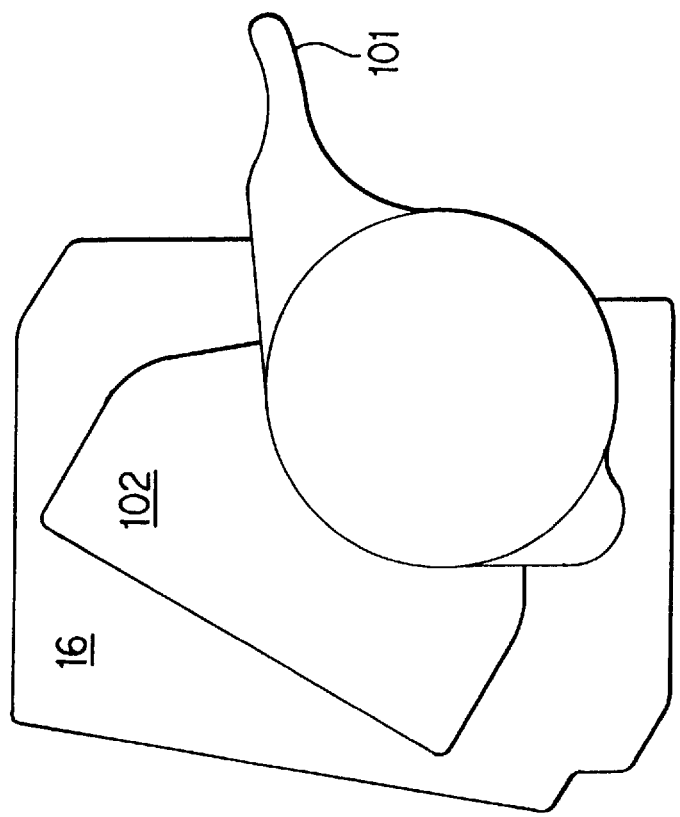
Figure 8A:
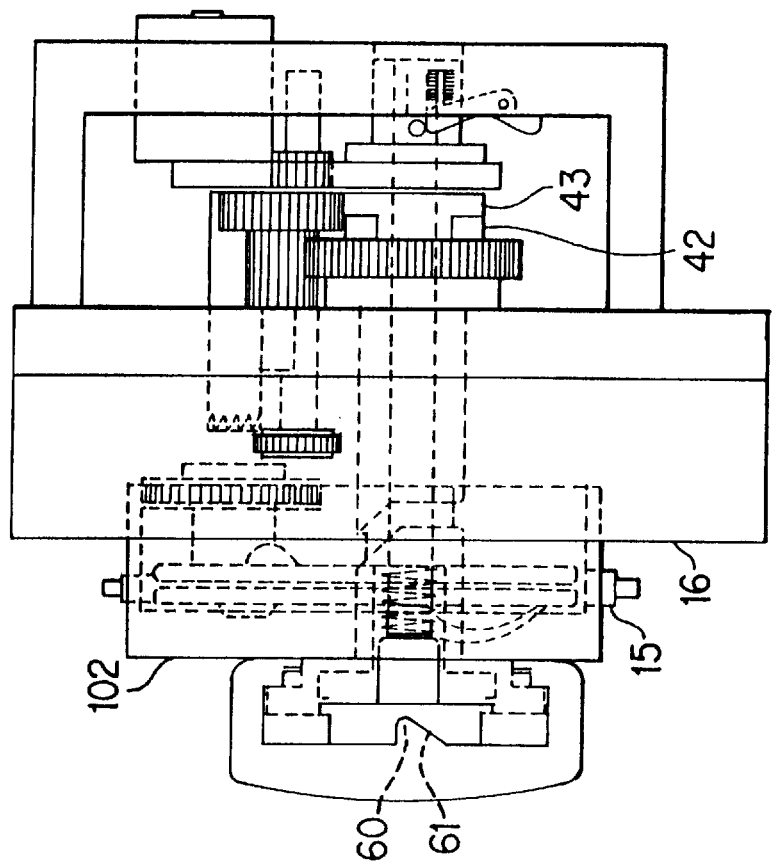

FIG. 8A shows the position of the mechanisms when door of the FIG. 5A with the door of the control unit ready to be closed.

FIG. 8B shows the position of the handle in the control unit of FIG. 8A.

Figure 9:
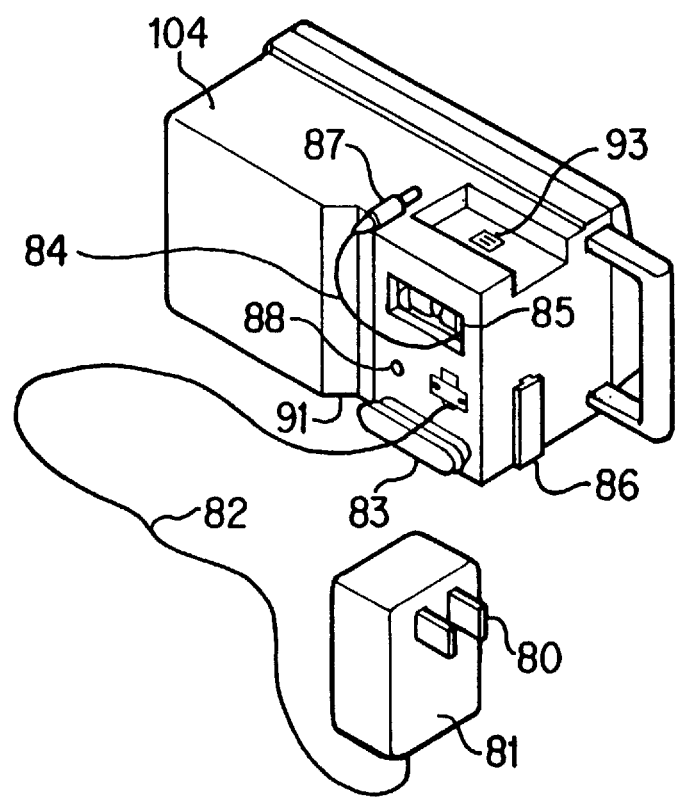

FIG. 9 shows a rear perspective view of a control unit according to a preferred embodiment of the invention.

Figure 10:
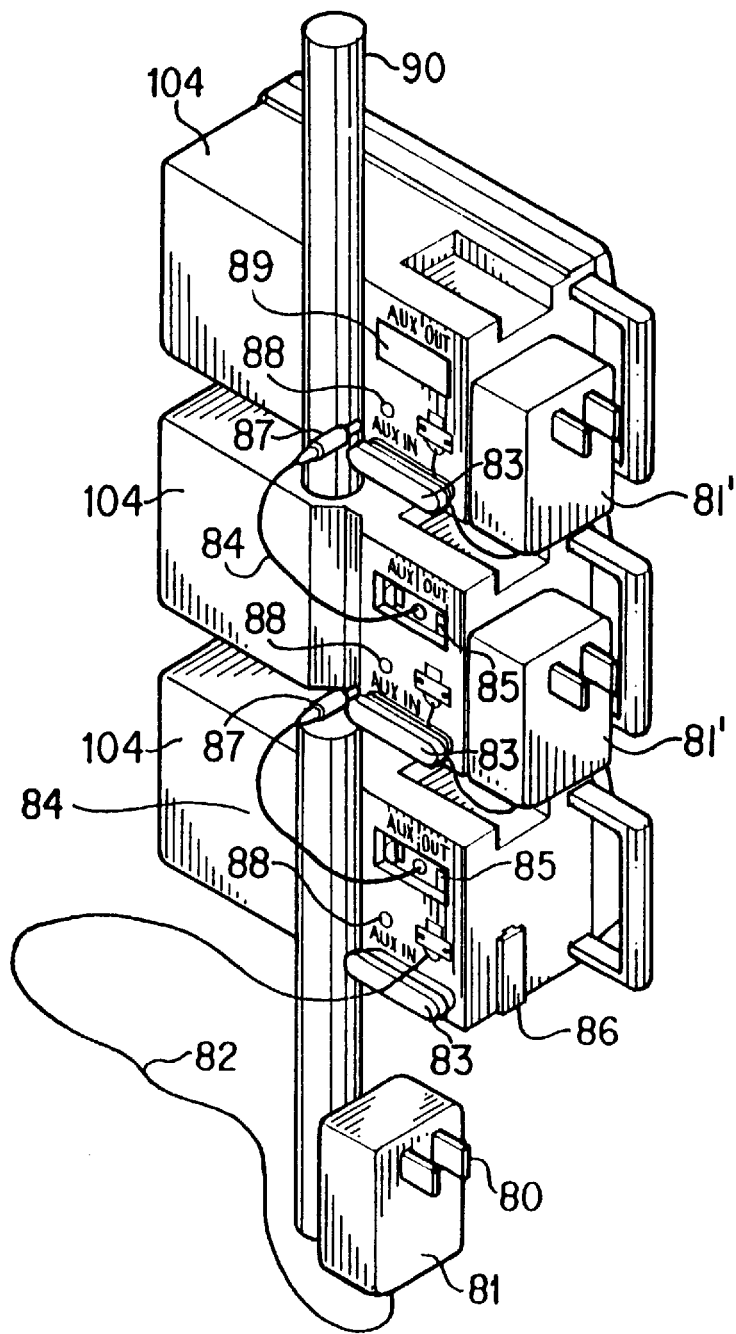

FIG. 10 shows a plurality of control units of the type shown in FIG. 9 mounted on an IV pole.

DETAILED DESCRIPTION OF THE SPECIFIC EMBODIMENTS

Figure 1A:
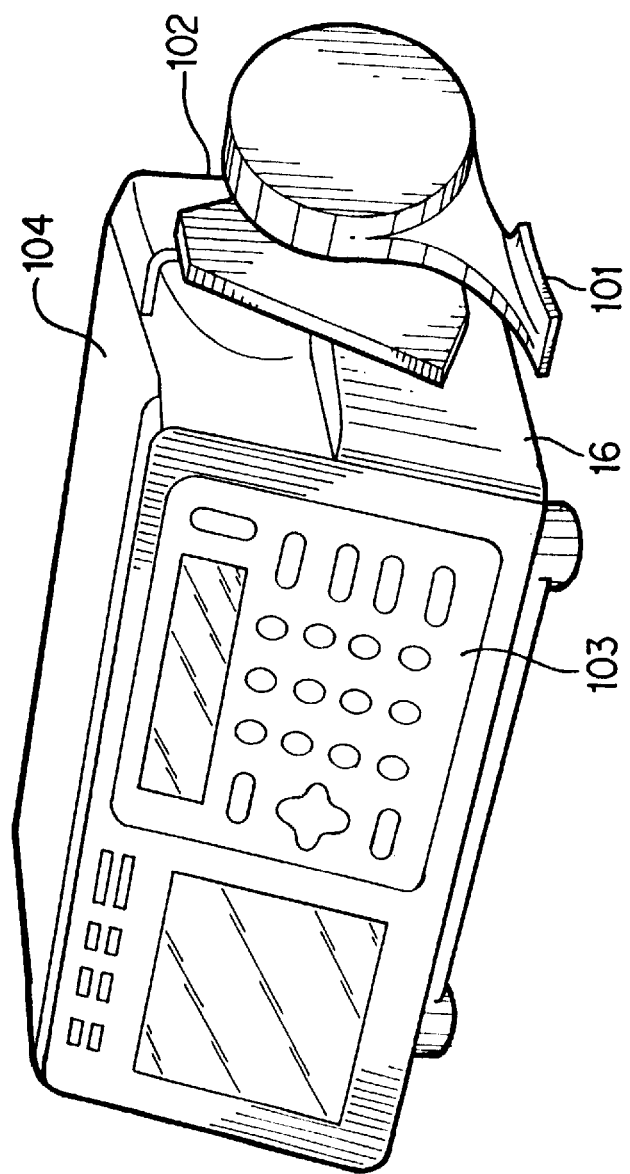
FIG. 1A shows a perspective view of the control unit according to one preferred embodiment of the present invention.
Figure 1B:
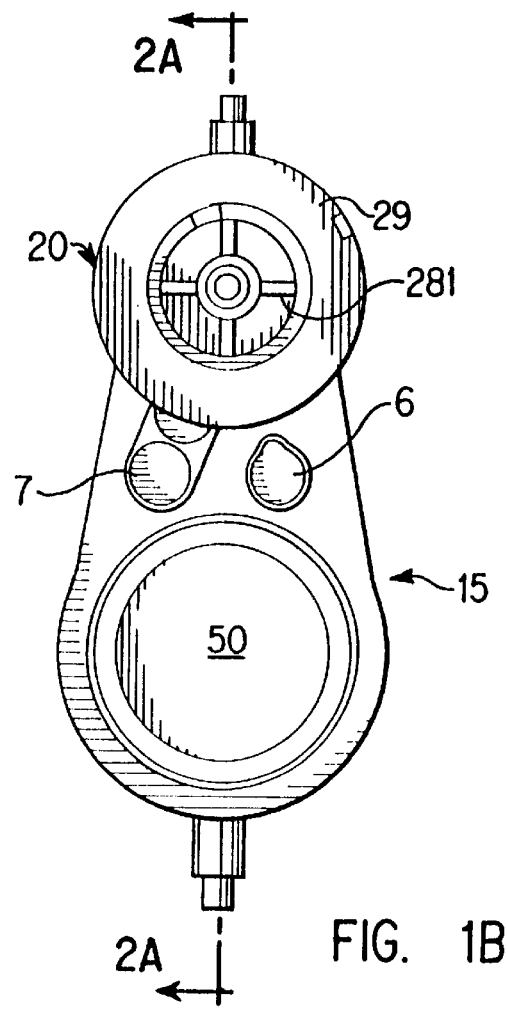
FIG. 1B shows an elevation view of a cassette that may be used in the control unit of FIG. 1, and in particular shows the front face of the cassette, which is mounted against the receiving surface of the control unit.

FIG. 1A shows a control unit according to a preferred embodiment of the present invention. The control unit receives a cassette, preferably of the type shown in FIG. 1B and described in above-referenced, concurrently filed application Ser. No. 08/478065 entitled "Cassette for Intravenous-Line Flow-Control System" for an invention by Houle and Larkins in a door 102, which by turning handle 101 can be moved towards and away from the housing 104 of the control unit. The door 102 preferably moves linearly, i.e., remaining parallel to the side wall 16, rather than in a swinging manner as though mounted on hinges. The cassette 15 is mounted in an IV line, which leads from a fluid source to a patient. The control unit's door 102 when closed presses the cassette 15 against a receiving surface of the control unit, which preferably includes means for actuating membrane-based valves 6, 7 on the cassette, for detecting air bubbles in a pressureconduction chamber 50 of the cassette and for measuring the amount of IV fluid in the pressure-conduction chamber. The control unit includes a user interface 103 including a keypad and a display, so that medical personnel using the control unit can program the desired flow rate and monitor the flow to the patient. The control unit also includes two mechanisms for turning a control wheel 20 of a valve in the cassette 15. One mechanism preferably engages ribs 281 on the control wheel 20 and controls the position of the wheel during normal operation with a stepper motor. The other mechanism preferably engages the circumference 29 of the wheel 20 when the control unit's door 102 is being opened.

While the cassette 15 is forced by the door 102 against the receiving surface, the control unit can actuate the membrane-based valves 6, 7, and the control wheel 20 so as to regulate precisely flow through the cassette. When the cassette 15 is removed, however, it is important that the flow through the cassette be automatically turned off so that a large flow of IV fluid does not get accidentally injected into the patient before the medical personnel can turn the control wheel 20 to close off the control valve in the cassette. It is often desirable to have as a feature to the door-opening mechanism, which is a handle 101 in the preferred embodiment, a mechanism for preventing the accidental opening of the door.

Figure 3C:
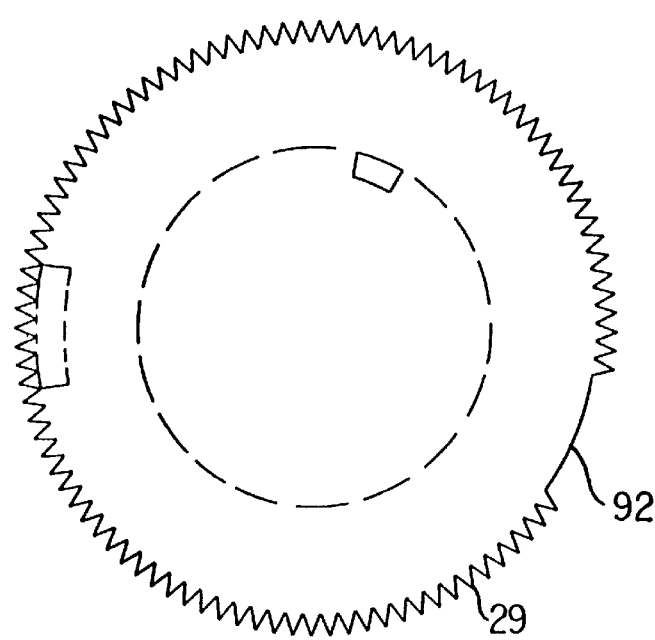
FIG. 3C shows the control wheel of a cassette from the rear of the cassette, when the wheel is in the off position.
Figure 2B:
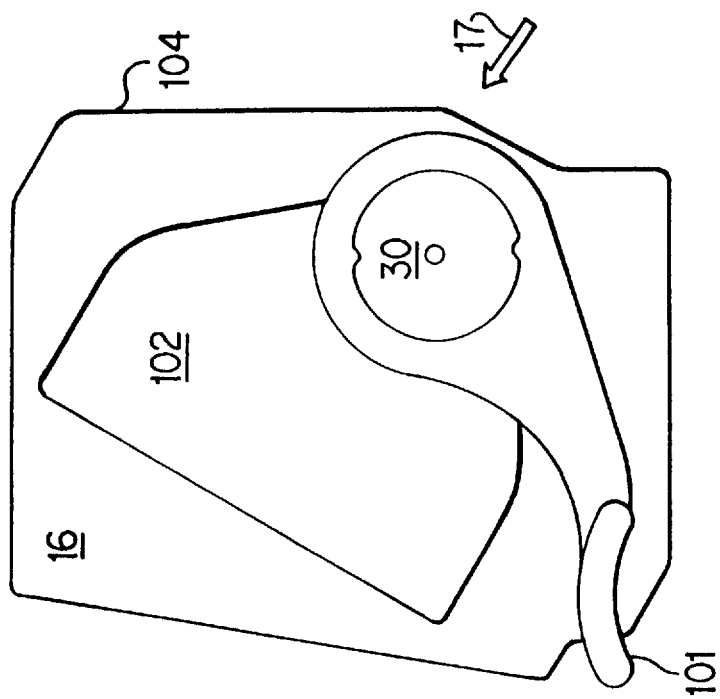
FIG. 2B shows the position of the handle of the FIG. 2A control unit during normal operation.
Figure 2A:
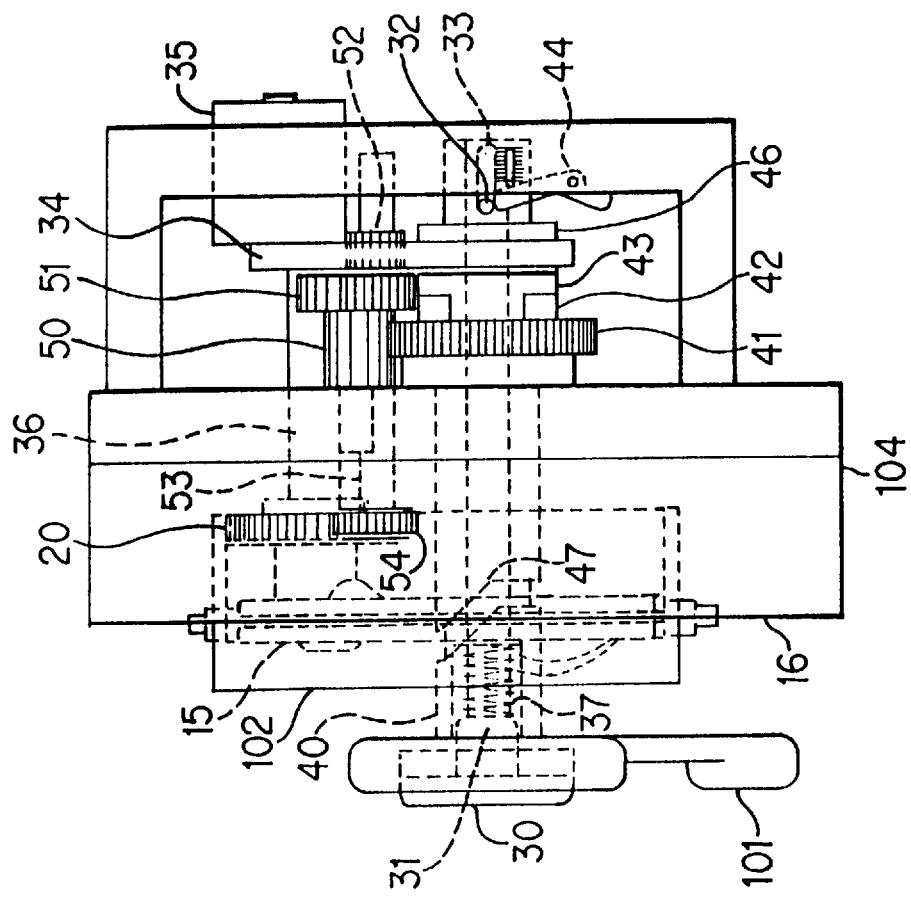
FIG. 2A shows the mechanisms of a control unit according to an alternative embodiment of the control unit during normal operation.

FIG. 2A shows mechanisms for preventing the free flow of IV fluid to the patient when the door 102 is opened and for preventing the accidental actuation of the handle 101 to open the door 102. During normal pumping operation by the control unit, when the cassette 15 is held against the receiving surface on the side wall 16 of the control unit, the position of the control wheel 20—and thus the resistance on flow through the cassette's stopcock-type control valve—is controlled by a stepper motor 35, which transmits torque to the control wheel 20 via a transmission member 36, which has a sprocketed end for engaging the ribs 281 on the control wheel 20. The control wheel 20 may contain a protruding tab or tabs that may be sensed by the control unit to indicate the position of the control wheel. A shut-off gear 54 is in communication with the circumference 29 of the control wheel 20, which preferably includes teeth (as shown in FIG. 3C) for better engagement between the gear 54 and the wheel 20. This shut-off gear 54 does not control or interfere with the movement of the control wheel 20 during normal pumping operation of the control unit, only during the process of opening the door 102. The shut-off gear 54 is connected to a shut-off shaft 53, which in turn is connected to final drive gear 52. During pumping, the final drive gear 52 is not in engagement with any other gear (except through the shaft 53), so that the shut-off gear 54, the shut-off shaft 53 and the final drive gear 52 are turned by the control wheel (which in turn is turned by the stepper motor 35) without providing any significant resistance to the rotation of the control wheel 20.

FIG. 2B shows a side elevation view of the control unit and the position of the handle 101 when the door is closed and the control unit is in its normal pumping mode. The cassette is mounted behind the door 102 (the lengths of IV tubing connected to the cassette would normally be visible entering and exiting the top and the bottom of the door 102) and pressed against the receiving surface on the side wall 16 of the control unit's housing 104. Arrow 17 indicates the view of the figures showing the internal mechanisms of the control unit (FIGS. 2A, 3A, 4A, 5A, 6A, 7A and 8A).

Figure 3B:
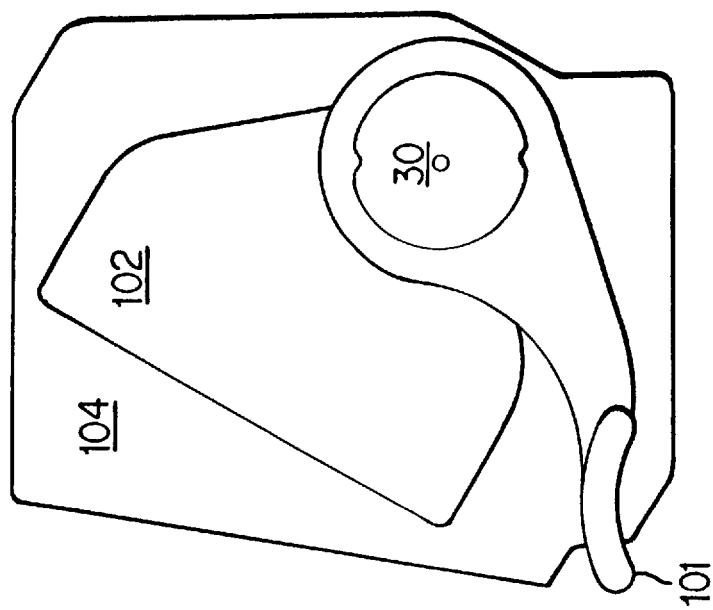
FIG. 3B shows the position of the handle in the control unit of FIG. 3A.
Figure 3A:
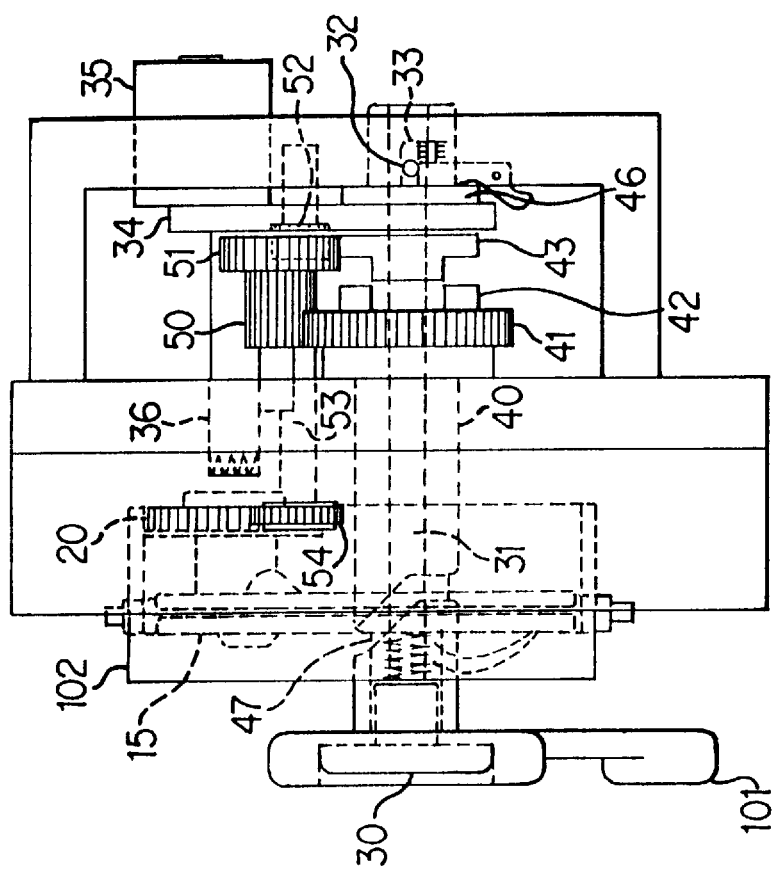
FIG. 3A shows the position of the mechanisms after the first step of opening the door of the FIG. 2A control unit.

FIG. 3A shows the effect of the first step in opening the door 102 of the control unit to remove the cassette; that step requires that the user press button 30. Normally, spring 37 forces the button to the left (as shown in FIG. 2A). The movement of button 30 to the right causes the button shaft 31 also to move to the right. The button shaft 31 is connected to a moveable mounting plate 34, to which is mounted the motor 35 and the sprocketed transmission member 36. The button shaft 31 can rotate with respect to the moveable mounting plate 34, but can move the plate 34 to the right (or left) by holding the plate 34 between the male key 43 and the bushing 46, both of which may be rigidly attached to the button shaft 31. Thus, the plate 34, motor 35 and the transmission member 36 also move to the right with the pressing of the button, and the transmission member thereby disengages from the control wheel 20. With the motor 35 disengaged from the control wheel 20, the motor 35 cannot interfere with the shut-off gear's turning of the control wheel 20.

Rotatably connected to the moveable mounting plate 34 are first and second idler gears 50, 51. With the pushing of the button 30, these idler gears 50, 51 also move to the right, so that the second idler gear 51 engages the final drive gear 52. The first and second idler gears 50, 51 are rigidly attached to each other. Since the first idler gear 50 is in communication with main gear 41, which in turn is attached to the handle 101 through the handle shaft 40, the shut-off gear 54 is in indirect engagement with the handle 101—through the shut-off shaft 53, the final drive gear 52, the second idler gear 51, the first idler gear 52, the main gear 41, the handle shaft 40.

The pushing of the button 30 also separates the female and male complementing keys 42, 43. The male key 43, as noted above, is connected to the button shaft 31, and thus moves to the right with the pushing of the button 30. The button shaft 31 has a pair of pins 32 (one of which is hidden from view). One of these pins 32 is normally prevented from moving downwardly by a spring-loaded catch 44 (see FIG. 2A). This arrangement prevents the button 30—and the button shaft 31 and the male key 43—from being turned in a clockwise (opening) direction as shown in FIG. 2B.

Thus, when male and female keys 43, 42 are engaged as shown in FIG. 2A, the female key 42 is also prevented from turning. Since the female key 42 is connected to the handle shaft 40, which in turn is connected to the handle 101, the handle 101 is prevented from turning in a clockwise (opening) direction while the male and female keys 43, 42 are engaged. A stop, which is not shown, may be used to prevent the handle 101 from rotating any further in the counter-clockwise (closing) direction once the handle is in the closed position shown in FIG. 2B. Thus, the pushing of the button 30 allows the handle 101 to be turned clockwise and thereby open the door 102.

When the male and female keys 43, 42 are disengaged, the pin 32 is urged into a slot 33 to prevent the button 30 and more importantly the male key 43 from rotating in either direction, so that the male and female keys 43, 42 can be re-engaged at the appropriate point later in the process.

At this point in the process, the button 30 has been pushed, but the handle 101 has not yet been turned, so that—as can be seen in FIG. 3B—the position of the handle is exactly the same as in FIG. 2B. However, at this point (i) the handle 101 can now be moved in the opening, clockwise direction, (ii) the transmission member 36 and thus the stepper motor 35 has been disengaged from the control wheel 20, and (iii) the shut-off gear 54 is (as will be discussed further below) in indirect engagement with the handle 101, so that when the handle 101 is now turned clockwise the control wheel 20 is turned to its closed position.

The handle 101 as noted above is connected to the handle shaft 40, which is hollow so as to accommodate the button shaft 31. The handle shaft 31 has a groove 47 around its circumference, and this groove 47 engages a pin (not shown) on the door 102. This groove is shaped so that as the handle 101 and its shaft 40 is turned a certain amount—say 80°—the door is not moved. Thereafter—for, say, the next 100° of movement of the handle 101—the door is opened. (Preferably, the handle shaft 40 has two identical grooves on opposite sides of the shaft 40 to ensure a smoother opening of the door 102.) During this first 80° of movement, the control wheel 20 is turned to the off position. As noted previously, at this point in the door-opening process, the handle 101 is indirectly connected to the shut-off gear (through the handle shaft 40, the main gear 41, the idler gears 50, 51, the final drive gear 52 and the shut-off shaft 53), so that the turning of the handle 101 results in the turning of the control wheel 20 at this point of the door-opening process.

To ensure that the shut-off gear 54 does not try to continue turning the control wheel 20 after the cassette's stopcock-type valve, to which the control wheel 20 is connected, a sector 92 of the control wheel's circumference 29 is left toothless, as shown in FIG. 3C. When the stopcock valve is completely closed, this toothless sector 92 is located at the position where the shut-off gear is located. Thus, when the stopcock valve is closed, the shut-off gear 54 loses engagement with the control wheel 20 because of the lack of teeth on the control wheel's circumference when the closed position is reached. Free flow of IV fluid to the patient is prevented, because the stopcock valve in the cassette 15 is closed before the cassette 15 can be removed from the control unit.

After the control wheel 20 is moved to the off position (which, in the depicted embodiment, should not take more than about 72°, even when the stopcock valve was initially in a completely open position) and the handle is moved the initial 80° (an additional 8° is added for safety), then the skewed portion of the handle shaft's groove 47 (or grooves) reaches the pin (or pins) connected to the door (but not shown in the figures) and causes the door 102 to be opened. Preferably, the skewed portion of the grooves 47 extends over a large sector (in the depicted embodiment, it is 100°) to ensure a smooth opening of the door without a great deal of torque having to be applied to the handle 101. This motion moves the door 101 about three-eighths to one-half inch to the left in the depicted embodiment.

During this 180° of clockwise, door-opening motion of the handle 101, the male and female keys 43, 42 are rotated with respect to each other; specifically, the female key 42 is rotated while the male key 43 maintains its position. Once these two complementing keys are rotated out of initial position with respect to each other, the two keys interfere with each other, so that the button 30 remains depressed, even if the user removes pressure (thumb pressure) from off of the button 30, and more importantly the motor's transmission member 36 remains disengaged from the control wheel 20, the shut-off gear 54 remains in indirect engagement with the handle 101.

Figure 4B:
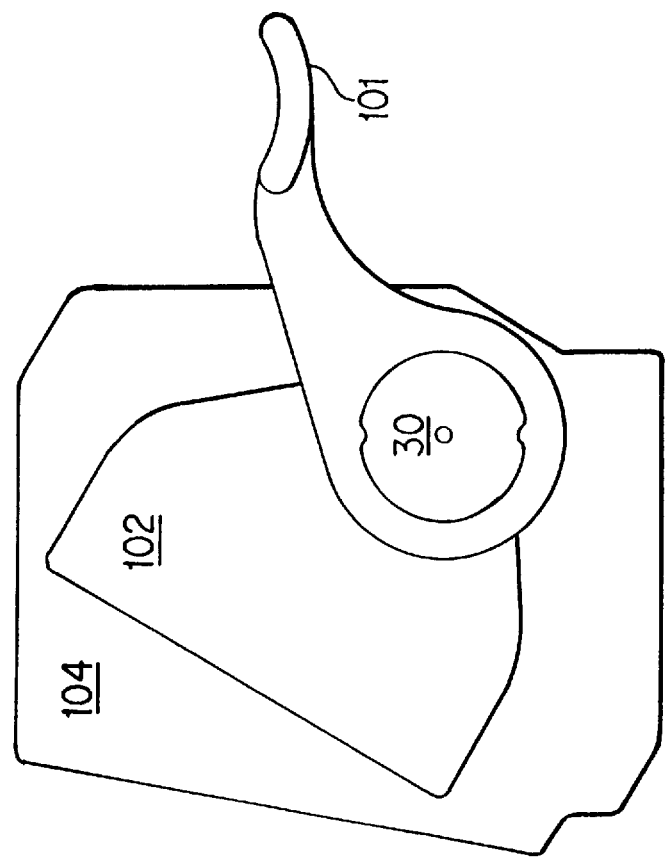
FIG. 4B shows the position of the handle in the control unit of FIG. 4A.
Figure 4A:
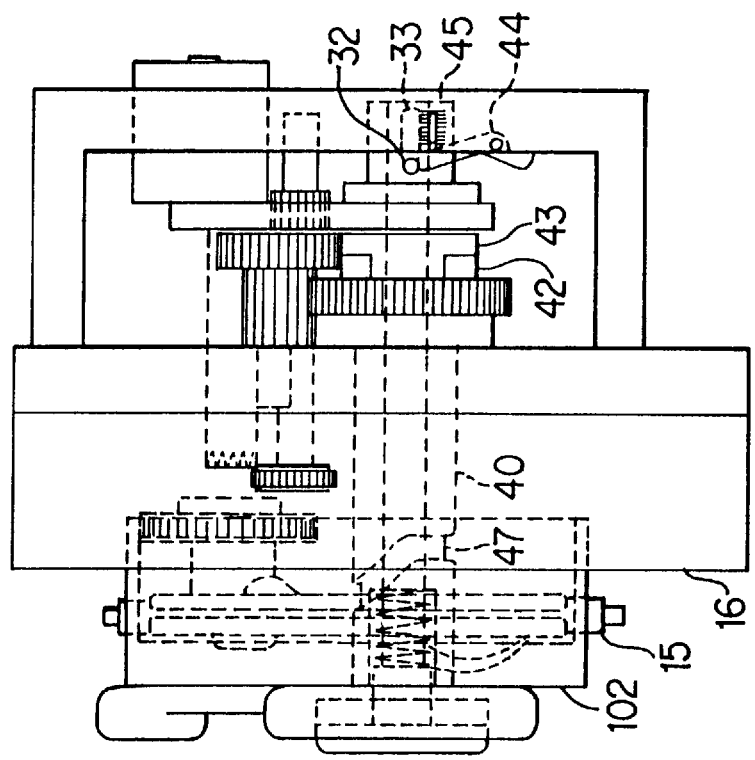
FIG. 4A shows the position of the mechanisms after the door of the FIG. 2A unit is fully opened.

Once the handle 101 is rotated the full 180°, as shown in FIG. 4B, the two keys 42 and 43 return to a complementing relationship, and the button 30 can thus spring back to its original position to the left, as shown in FIG. 4A. This springing back to the left by the button 30 causes the motor 35 and transmission member 36 to move left, back to their original position, and causes the shut-off gear 54 to lose its indirect engagement with the handle 101 (because the final drive gear 52 becomes disengaged from the second idler gear 51). With the handle 101 in the position shown in FIG. 4B, the cassette 15 can be removed from the control unit.

The cassette 15 (the same cassette or a different cassette) can be reinserted behind the door 102 of the control unit, when it is in the position shown in FIGS. 4A and 4B. To close the door 102 and force the cassette 15 against the receiving surface of side wall 16, the handle 101 is simply turned counter-clockwise. The button 30 and its shaft 31 rotates with the handle 101 and its shaft 41. The spring-loaded catch 44 permits rotation of the button shaft 31 in the counter-clockwise direction without the need for pushing the button 31. Thus, the handle shaft 40 can also rotate counter-clockwise, even though the complementing male and female keys 43, 42 (which are attached respectively to the button and handle shafts 31, 40) are engaged.

In the FIG. 1A embodiment of the control unit, no button is visible to the user. It will be seen from FIG. 5A, which shows the mechanisms of the FIG. 1A embodiment in the normal closed position, that a button 30 is present inside the hub of the handle 101. The handle's hub has a male cam surface 60, while the button 30 has a female cam surface 61. When the handle 101 is first turned from its initial, closed position, shown in FIG. 5B, to the position shown in FIG. 6B, the handle's cam 60 forces the button 30 to the right, as shown in FIG. 6A (which corresponds to the handle position of FIG. 6B). This motion has the same effect as pushing the button in the FIG. 2A control unit embodiment, and it will be appreciated that the positions of the mechanisms to the right of side wall 16 in FIG. 6A are virtually identical to the positions of the same mechanisms to the right of the side wall 16 in the FIG. 3A embodiment. (Likewise, it will be appreciated that the mechanisms to right of the side wall 16 in the fully closed position shown in FIG. 5A are virtually identical to the positions of the same mechanisms to the right of the sidewall 16 in FIG. 2A, which also shows the control unit in the fully closed position.)

As just noted, FIGS. 5A and 5B show the positions of the mechanisms and the handle 101 when the control unit is in its normal pumping mode. To remove the cassette 16, the user—instead of pushing a button and then turning the handle as in the FIG. 2A embodiment—simply turns the handle. Thus, the FIG. 5A embodiment lacks the feature of the FIG. 2A embodiment that prevents the accidental opening of the door; on the other hand, the FIG. 5A embodiment is much easier and quicker to use, and thus may be more appropriate if the chances of accidental opening are considered very small and especially if the ability to quickly and efficiently remove and change IV lines, in emergency situations, for instance, is considered more important.

In the FIG. 5A embodiment, the handle 101 is not rigidly attached to the handle shaft 40. Instead, the handle 101 can turn sufficiently to cause the cam 60 to push button 31, before the handle reaches a point where it engages the handle shaft 40. Thus, when the handle 101 is turned from the position shown in FIG. 5B to the position shown in FIG. 6B, the handle shaft 40 does not turn, and in fact it cannot turn, because until the handle reaches the position shown in FIG. 6B, the female key 42 is still engaged in complementary relationship with the male key 43, which is in turn prevented from moving in the opening (clockwise) direction by the spring-loaded catch 44 holding the pin 32. Once the handle 101 reaches the position of FIG. 6B, the button 30 is pushed to the right, thereby disengaging the male and female keys 43, 42.

In the handle position shown in FIG. 6B, and the corresponding mechanism position depicted in FIG. 6A, (i) the handle shaft 40 can now be moved in the opening, clockwise direction, (ii) the transmission member 36 and thus the stepper motor 35 has been disengaged from the control wheel 20, so that the motor cannot lock the control wheel 20 in place, and (iii) the shut-off gear 54 is in indirect engagement with the handle 101, so that when the handle 101 is now turned clockwise the control wheel 20 is turned to its closed position (and thus, the control unit's internal mechanism are in the same position as the internal mechanisms shown in FIG. 3A). When the handle 101 is turned to the position shown in FIG. 7B, the shut-off gear 54 has already turned the control wheel 20 to the off position (thereby preventing free flow), and the door 102 is opened (i.e., moved to the left), allowing the cassette 15 to removed from the receiving surface on the control unit's side wall 16. The male and female keys 43, 42 are not in alignment, however. The keys 42, 43 did pass an alignment orientation while the handle was being turned from the FIG. 6B position to the FIG. 7B position, but since the handle's cam 60 was continuing to push the button 30 to the right, the keys 42, 43 were unable to engage. By turning the handle back in the counter-clockwise direction, to the position shown in FIG. 8B, the keys 42, 43 come into alignment, while the cam surfaces 60, 61 of the handle also come into alignment and thus engage, thereby allowing the keys 42, 43 to also engage. In this position, a cassette 15 may again be inserted into the door 102 of the control unit, and the handle 101 may be turned further counter-clockwise to close the door 102 and force the cassette 15 against the receiving surface of the side wall 16.

The control unit, of course, requires a power supply in order to provide the power necessary to actuate membrane-based valves 6, 7 on the cassette (shown in FIG. 1B), to detect air bubbles in a pressure-conduction chamber 50 of the cassette and to measure and control the amount of IV fluid being pumped to the patient, including the power necessary to run the motor 35. Prior-art pumping units used heavy-duty cords to attach to an AC power outlet, and they also included an internal battery so that when the unit was unplugged from the AC outlet the unit could continue to function. Prior-art pumping units also included the ability to daisy-chain—that is, to plug into a neighboring unit, which was attached to either an AC outlet or to yet another unit, and at some point the chain was connected to an AC outlet. Daisy-chaining the AC power was convenient, since it was often necessary to mount several pumping units to the same IV pole to control the flow through several IV lines to the same patient.

FIG. 9 shows a preferred, novel power supply system for the control unit of the present invention. Instead of using a heavy-duty AC power cord, the unit uses a wall plug-in AC-DC adapter 81, which has prongs for connecting to the AC outlet. The adapter 81, which includes a step-down transformer, is connected to the unit's housing 104 by a thin DC cord 82, thereby avoiding the use of the bulky AC power cords. The unit also includes a second DC cord 84 with a DC plug 87 for providing power to a second unit. Both cords 82, 84 include organizers 83, 85, to hold the cord when it is not being used. Attachment means 86 are also included on the housing 104 for holding the adapter 81 when it is not in use. The control unit also includes a receptacle 88 for receiving a DC plug, and DC power from another unit. An internal battery is located inside the housing 104, so that the unit may work even if its adapter 81 is not connected to a wall outlet, and its receptacle 88 not connected to another unit. Although the internal battery is recharged whenever the unit is connected to a wall outlet, either directly or through another unit, the internal battery can run down. In order to provide emergency power in such a situation when an AC outlet is not convenient, the unit further includes a receptacle 93 for an external battery pack. In one preferred method of using the unit, an external battery pack is kept attached to receptacle 93, and the internal battery is only used in emergencies. When the external battery pack runs down, and no AC outlet is conveniently available, the external battery pack may be removed and replaced by a fully charged battery pack; the internal battery pack provides the interim power while the external battery packs are being switched.

The back of the unit's housing 104 includes pole-grasping means 91, so that the unit may be mounted on an IV pole. FIG. 10 shows three units mounted to an IV pole 90. The bottom unit obtains its power through cord 82 from its adapter 81, which is plugged into an AC outlet. By plugging the bottom unit's DC plug 87 into the middle unit's receptacle 88, the second cord 84 of the bottom unit provides power to the middle unit. Likewise, by plugging the middle unit's DC plug 87 into the top unit's receptacle 88, the cord 84 of the middle unit provides power to the top unit. Since the DC plug of the top unit is not used, it and its cord may be stored on an organizer, which may be hidden under a panel 89. The adapters 81' of the middle and top units are not used and are therefore stored on the side of the housing 104, which has attachment means similar to the attachment means 86 on the bottom unit. Other forms of attachment means 86 may be used, such as the fastening means commonly sold under the trademark "Velcro." Other forms of organizers 83, 85 may also be used, such as spring-loaded coiling systems, which can automatically retract a cord inside the housing 104 so as to leave only the adapter 81 or the DC plug 87 visible.

The daisy-chain cords 84 may include additional wires to permit the communication of information between he units. This feature is important if the patient requires a drug therapy where the multiple medications or other fluids should be given in a particular sequence. This feature is also useful if medical personnel wish to download all the information about the IV fluid delivered to the patient, e.g. amount and time of each fluid; this downloading may be accomplished by accessing a single unit, which has access to the information in the other units, instead of having to access each unit separately. This feature is also useful for providing software code to multiple units at the same time, such as when a new drug-delivery protocol is to be programmed into the units, or even at the factory for loading software into several units at the same time.

Although the invention has been described with reference to several preferred embodiments, it will be understood by one of ordinary skill in the art that various modifications can be made without departing from the spirit and the scope of the invention, as set forth in the claims hereinbelow.

What is claimed is:

1. An intravenous-line flow-control system for receiving a disposable cassette disposed in the intravenous line and preventing the free flow of intravenous fluid through the cassette as the cassette is removed from the system, the system comprising:

a housing having a receiving surface against which the cassette is placed;

door means, connected to the housing, for holding the cassette against the receiving surface when the door means is closed and for allowing removal of the cassette when the door means is open;

door-opening means for causing, upon actuation by a user, the opening of the door means;

turning means for turning a rotatable control valve on the cassette in order to restrict variably the flow of fluid through the cassette, the turning means including a stepper motor and a transmission member, capable of being turned by the stepper motor and capable, when the door means is closed, of engaging the control valve to transmit torque from the motor to the control valve, the transmission member being movably mounted in the housing;

motor-disengagement means, connected to the door-opening means, for moving, when the door-opening means is being actuated but while the cassette is still held against the receiving surface, at least the transmission member of the turning means with respect to the housing from a first position to a second position away from the cassette's control valve so that the transmission member becomes disengaged from the control valve; and shut-off means, connected to the door-opening means, for engaging, when the door-opening means is being actuated but while the cassette is still held against the receiving surface, the cassette's control valve and turning the control valve to its closed position.

2. A system according to claim 1, wherein the door-opening means includes a handle that may be turned by the user, the handle being connected to the door means so that, when the handle is turned sufficiently, the door means opens.

3. A system according to claim 2, wherein the motor-disengagement means includes a button that must be pushed before the handle is turned enough to open the door means, wherein the button is connected to the transmission member so that when the button is pushed the turning means is moved to the second position and the transmission member becomes disengaged from the control valve.

4. A system according to claim 3, wherein the motor-disengagement means includes means to keep the turning means in the second position while the handle is being turned to open the door means.

5. A system according to claim 4, wherein after the door means opens, the motor-disengagement means allows the turning means to return to the first position.

6. A system according to claim 5, wherein the motor-disengagement means includes first and second complementing keys, the first key being attached to and rotating with the handle, the second key being attached to and moving with the button, so that (i) when the door means is closed, the first and second keys are in complementary engagement, (ii) when the button is pushed, the first and second keys become disengaged, and (iii) when the handle is turned to open the door means, the first key is turned with respect to the second key, so that the keys are in interfering relation with each other.

7. A system according to claim 6, wherein the first and second keys are shaped so that, when the door is fully opened, the first and second keys return to complementary engagement with each other.

8. A system according to claim 7, wherein the handle is prevented from moving sufficiently to open to door means unless and until the button is pushed to disengage the first and second keys.

9. A system according to claim 8, wherein the handle includes cam means for pushing the button as the handle is first turned to open the door means.

10. A system according to claim 9, wherein the stepper motor is movably mounted in the housing, and the motor-disengagement means causes the movement of the stepper motor with the transmission member from the first to the second position, when the door means is being actuated.

11. A method for controlling flow through an intravenous-line having a cassette disposed therein, and preventing the free flow of intravenous fluid through the cassette as the cassette is removed from a control unit, the method comprising the steps of:

provR providing on the cassette a rotatable valve with a control wheel having a circumference, wherein the control wheel has first and second engaging means, the first engaging means including a plurality of teeth closely located with respect to each other and evenly distributed around the circumference of the control wheel, except for a sector of the circumference that lacks teeth;

providing a stepper motor in the control unit for controlling the setting of the control wheel, by engaging the control wheel's second engaging means, in order to restrict variably the flow of intravenous fluid through the cassette;

providing a motor-disengagement mechanism in the control unit for disengaging the stepper motor from the control wheel's second engaging means; and providing a shut-off mechanism in the control unit for turning the control wheel to close the valve, after the stepper motor is disengaged from the control wheel's second engaging means but before the cassette can be removed the shut-off mechanism having a gear for engaging the control wheel's first engaging means;

wherein the sector of the control wheel's circumference that lacks teeth is located so that, when the valve is in its fully closed position, the sector lacking teeth is adjacent the shut-off mechanism's gear, so that the shut-off mechanism does not continue turning the control wheel after the valve is fully closed.

12. A system for controlling flow through an intravenous-line, and preventing the free flow of intravenous fluid through the line cassette as the line is removed from the system, the system comprising:

a cassette having a rotatable valve with a control wheel having a circumference, wherein the control wheel has first and second engaging means, the first engaging means including a plurality of teeth closely located with respect to each other and evenly distributed around the circumference of the control wheel, except for a sector of the circumference that lacks teeth;

a control unit;

turning means, in the control unit, for controlling the setting of the control wheel, by engaging the control wheel's second engaging means, in order to restrict variably the flow of intravenous fluid through the cassette;

motor-disengagement means, in the control unit, for causing the turning means to disengage the control wheel's second engaging means; and shut-off means, in the control unit, for turning the control wheel to close the valve, after the turning means is disengaged from the control wheel's second engaging means but before the cassette is removed from the control unit, the shut-off means having a gear for engaging the control wheel's first engaging means;

wherein the sector of the control wheel's circumference that lacks teeth is located so that, when the valve is in its fully closed position, the sector lacking teeth is adjacent the shut-off means's gear, so that the shut-off means does not continue turning the control wheel after the valve is fully closed.

* * * * *

UNITED STATES PATENT AND TRADEMARK OFFICE
CERTIFICATE OF CORRECTION

PATENT NO. : 5,772,637
DATED : June 30, 1998
INVENTOR(S) : Heinzmann et al.

It is certified that error appears in the above-identified patent and that said Letters Patent is hereby corrected as shown below:

Col. 11, line 42, change "removed the shut-off" to --removed from the control unit, the shut-off--

Signed and Sealed this

Twenty-ninth Day of December, 1998

Attest:

BRUCE LEHMAN

Attesting Officer

Commissioner of Patents and Trademarks